United States Patent
Rezai et al.

(10) Patent No.: US 8,583,229 B2
(45) Date of Patent: Nov. 12, 2013

(54) METHODS OF TREATING MEDICAL CONDITIONS BY NEUROMODULATION OF THE SYMPATHETIC NERVOUS SYSTEM

(75) Inventors: Ali Rezai, Bratenhal, OH (US); Mehdi Ansarinia, Las Vegas, NV (US)

(73) Assignee: The Cleveland Clinic Foundation, Cleveland, OH (US)

( * ) Notice: Subject to any disclaimer, the term of this patent is extended or adjusted under 35 U.S.C. 154(b) by 220 days.

(21) Appl. No.: 12/981,395

(22) Filed: Dec. 29, 2010

(65) Prior Publication Data
US 2011/0152974 A1 Jun. 23, 2011

Related U.S. Application Data

(60) Division of application No. 11/121,006, filed on May 4, 2005, now Pat. No. 7,877,146, which is a continuation-in-part of application No. 10/495,766, filed on May 5, 2004, now Pat. No. 7,778,704, which is a continuation-in-part of application No. 10/001,923, filed on Oct. 23, 2001, now Pat. No. 6,885,888.

(51) Int. Cl.
*A61N 1/00* (2006.01)

(52) U.S. Cl.
USPC .......................................................... 607/9

(58) Field of Classification Search
USPC ............................................................ 607/62
See application file for complete search history.

(56) References Cited

U.S. PATENT DOCUMENTS

| | | |
|---|---|---|
| 5,178,156 A | 1/1993 | Takishima et al. |
| 5,645,570 A | 7/1997 | Corbucci |
| 6,006,134 A | 12/1999 | Hill et al. |
| 6,058,331 A | 5/2000 | King |
| 6,104,957 A | 8/2000 | Alo et al. |
| 6,141,590 A | 10/2000 | Renirie et al. |
| 6,198,970 B1 | 3/2001 | Freed et al. |
| 6,251,126 B1 | 6/2001 | Ottenhoff et al. |
| 6,266,564 B1 | 7/2001 | Hill et al. |
| 6,292,695 B1 | 9/2001 | Webster, Jr. et al. |
| 6,356,786 B1 | 3/2002 | Rezai et al. |
| 6,356,787 B1 | 3/2002 | Rezai et al. |
| 6,438,723 B1 | 8/2002 | Kalliojarvi |
| 6,633,779 B1 | 10/2003 | Schuler et al. |
| 6,832,114 B1 * | 12/2004 | Whitehurst et al. ............ 607/40 |

(Continued)

FOREIGN PATENT DOCUMENTS

RU 2 108 817 C1 4/1998

OTHER PUBLICATIONS

Gromova et al., "Sinusoidal Modulated Currents in Comprehensive Treatment of Children with Bronchial Asthma", *Mosco Institute of Pediatrics and Child Surgery of the Ministry of Health of RSFSR*, undated.

(Continued)

*Primary Examiner* — Christopher D Koharski
*Assistant Examiner* — Nadia Ahmad
(74) *Attorney, Agent, or Firm* — Tarolli, Sundheim, Covell & Tummino LLP

(57) ABSTRACT

The present invention is directed to systems and methods for treating respiratory or pulmonary medical conditions by neuromodulation of a target site of the sympathetic nervous system and preferably a target site in communication with a sympathetic nerve chain. A system for treating a respiratory or pulmonary medical condition incorporating a closed-loop feedback system is also provided.

10 Claims, 7 Drawing Sheets

(56) References Cited

U.S. PATENT DOCUMENTS

| | | |
|---|---|---|
| 7,149,574 B2 | 12/2006 | Yun et al. |
| 7,477,944 B1 | 1/2009 | Whitehurst et al. |
| 7,599,736 B2 | 10/2009 | DiLorenzo |
| 7,689,276 B2 | 3/2010 | Dobak |
| 2002/0010495 A1 | 1/2002 | Freed et al. |
| 2002/0107553 A1 | 8/2002 | Hill et al. |
| 2002/0165586 A1 | 11/2002 | Hill et al. |
| 2003/0004549 A1 | 1/2003 | Hill et al. |
| 2003/0045909 A1 | 3/2003 | Gross et al. |
| 2003/0093128 A1 | 5/2003 | Freed et al. |
| 2003/0100924 A1 | 5/2003 | Foreman et al. |
| 2003/0181951 A1 | 9/2003 | Cates |
| 2003/0181958 A1 | 9/2003 | Dobak, III |
| 2003/0181959 A1 | 9/2003 | Dobak, III |
| 2004/0030362 A1 | 2/2004 | Hill et al. |
| 2004/0230251 A1 | 11/2004 | Schuler et al. |
| 2004/0243182 A1 | 12/2004 | Cohen et al. |
| 2004/0249416 A1 | 12/2004 | Yun et al. |
| 2005/0021092 A1 | 1/2005 | Yun et al. |
| 2005/0021102 A1 | 1/2005 | Ignagni et al. |
| 2005/0075702 A1 | 4/2005 | Shafer |
| 2009/0216286 A1 | 8/2009 | DiLorenzo |

OTHER PUBLICATIONS

Gudovsky et al., "Surgical Treatment of Bronchial Asthma", *Surgery*, 7 (2002).

Karashurov et al., "Evolution of Surgical Treatment of Bronchial Asthma", *Khirugiia*, pp. 57-60 (1999).

Karashurov et al., "Radio Frequency Electrostimulation of the Gangliated Cord of the Sympathetic Nerve in Patients with Bronchial Asthma", *Surgery*, 1 (2000).

Matsumoto et al., "Effective Sites by Sympathetic Beta-Adrenergic and Vagal Nonadrenergic Inhibitory Stimulation in Constricted Airways", *Am. Rev. Respir. Dis.*, 132:1113-7 (1985) (Abstract Only).

\* cited by examiner

METHODS OF TREATING MEDICAL CONDITIONS BY NEUROMODULATION OF THE SYMPATHETIC NERVOUS SYSTEM

CROSS-REFERENCE TO RELATED APPLICATIONS

The present application is a divisional application of U.S. Ser. No. 11/121,006, filed on May 4, 2005, now U.S. Pat. No. 7,877,146 which is a continuation-in-part of U.S. application Ser. No. 10/495,766, filed on May 5, 2004, now U.S. Pat. No. 7,778,704, which is a continuation-in-part of U.S. Ser. No. 10/001,923, filed on Oct. 23, 2001, now U.S. Pat. No. 6,885,888. All of the above-referenced applications are incorporated by reference herein.

FIELD OF THE INVENTION

The present invention relates to methods of treating medical conditions by electrical and/or chemical neuromodulation of target sites in the sympathetic nervous system.

BACKGROUND OF THE INVENTION

Neuromodulation involves an array of therapeutic approaches applied to the brain, cranial nerves, spinal cord and all associated nerves and neural structures in the human body to treat various human disorders. Neuromodulation can involve lesioning, electrical stimulation/modulation, chemical stimulation/modulation including gene therapy and administration of stem cells. Electrical stimulation of neural tissue is becoming an increasingly preferred form of therapy for certain neurological conditions and disorders where existing therapies generate intolerable side effects, require repeated administration of treatment, or are simply ineffective in a subset of patients. Electrical stimulation provides distinct advantages over surgical lesioning techniques since electrical stimulation is a reversible and adjustable procedure that provides continuous benefits as the patient's disease progresses and the patient's symptoms evolve.

Currently, electrical stimulation of peripheral nerves and the spinal cord is approved for treatment of neuropathic pain. With respect to deep brain targets, electrical stimulation of the subthalamic nucleus and the globus pallidus interna is approved for treatment of Parkinson's disease and electrical stimulation of the ventral intermediate nucleus is approved for treatment of essential tremor.

There remains a need for further forms of neuromodulation to treat these and other disorders.

SUMMARY OF THE INVENTION

In an embodiment, the present invention provides a system for treating a medical condition comprising a therapy delivery device for positioning at a target site of the sympathetic nervous system and a controller in communication with the therapy delivery device for enabling the therapy delivery device to deliver therapy to the target site to treat the medical condition. In a preferred embodiment, the target site is in communication with the sympathetic nerve chain. The therapy delivery device can be a stimulation lead for delivering electrical neuromodulation or a drug port for delivering chemical neuromodulation to the target site.

The present invention also provides a system for treating a medical condition comprising a therapy delivery device for applying a therapy signal on a target site in the sympathetic nervous system. The system also include a sensor for detecting a bodily activity associated with the medical condition and generating a sensor signal. The system also includes a controller in communication with the therapy delivery device and the sensor for activating the therapy delivery device to initiate application of the therapy signal to the target site or to adjust application of the therapy signal to the target site in response to the sensor signal. The therapy signal can be an electrical signal in embodiments where the therapy delivery device is a stimulation lead and a chemical signal in embodiments where the therapy delivery device is a drug port.

The present invention also provides a method for treating a medical condition comprising placing a therapy delivery device on a target site of the sympathetic nervous system, preferably a target site in communication with a sympathetic nerve chain, and activating the therapy delivery device to deliver therapy to the target site to treat the medical condition.

The medical conditions that can be treated by the systems and methods of the present invention include skeletal, immunological, vascular/hemotological, muscular/connective, neurological, visual, auditory/vestibular, dermatological, endocrinological, olfactory, cardiovascular, genitourinary, psychological, gastrointestinal, respiratory/pulmonary, inflammatory and neoplastic medical conditions.

The present invention also provide methods of stabilizing and optimizing bodily functions perioperatively and/or postoperatively by stimulating a target site in communication with a sympathetic nerve chain.

DETAILED DESCRIPTION OF THE INVENTION

Figure 1:
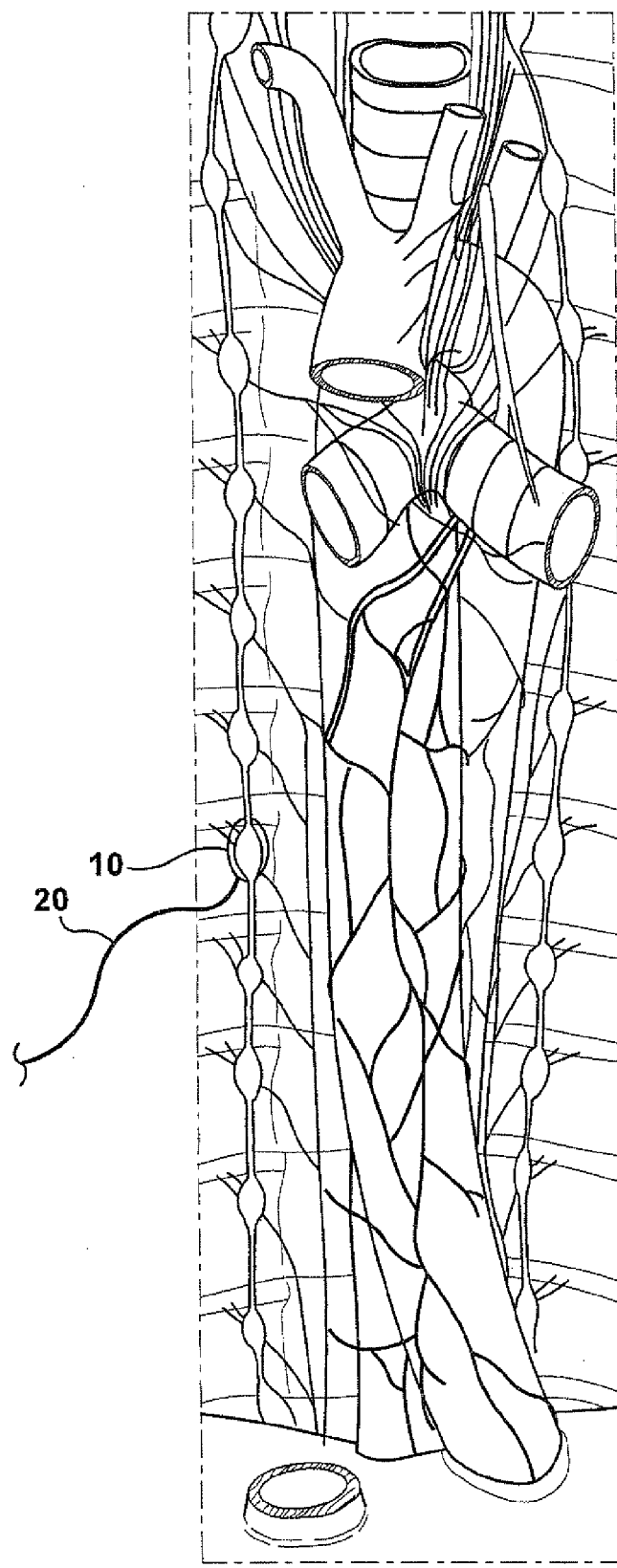
FIG. 1 is a therapy delivery device positioned at a target site of the sympathetic nervous system according to systems and methods of the present invention.

The present invention provides systems and methods for treating medical conditions by neuromodulation of a target site of a sympathetic nervous system and preferably neuromodulation of a target site in communication with a sympathetic nerve chain.

The sympathetic nervous system is a division of the autonomic nervous system and includes the sympathetic nerve chains and its associated direct and indirect input and output nerve branches, nerve clusters, nerve aggregates, and nerve plexuses located, for example, in the skull, base of the skull, neck, thoracic, abdominal, and pelvic cavities, and their associated arterial and venous structures. The sympathetic nerve chain (also known as the sympathetic nerve trunk) is a long ganglionated nerve strand along each side of the vertebral column that extends from the base of the skull to the coccyx. Each sympathetic nerve chain is connected to each spinal nerve by gray rami and receives fibers from the spinal cord through white rami connecting with the thoracic and upper lumbar spinal nerves. A sympathetic nerve chain has paravertebral ganglia that are connected by a paravertebral sympathetic chain. Target sites in communication with the sympathetic nerve chain, according to the present invention, are target sites in the nervous system having fibers that project to and/or from the sympathetic nerve chain. Examples of such target sites include the superior cervical, middle cervical, vertebral, inferior cervical and cervicothoracic ganglia, spinal cord segments T1 to L3; sympathetic ganglia (including paravertebral ganglia and prevertebral ganglia), paravertebral sympathetic chain, thoracic and lumbar sympathetic ganglia, nerve plexuses in communication with sympathetic ganglia, dorsal roots, ventral roots, dorsal root ganglia, dorsal rami, ventral rami, white rami communicans, gray rami communicans, and recurrent meningeal branches, all emerging from spinal cord segments T1 to L3; T1 to L3 spinal nerves; and any combination of the above from one or both of the sympathetic nerve chains. Thoracic and lumbar ganglia and prevertebral ganglia and their associated sympathetic structures include the cardiac, celiac, mesenteric (superior and inferior), renal, hypogastric, and intermesenteric (abdominal aortic) ganglia as well as ganglia associated with glands such as hepatic or adrenal glands. Nerve plexuses include prevertebral plexuses such as the superior and inferior hypogastric (pelvic) plexus. Target sites also include the thoracic, lumbar, and sacral splanchnic nerves. The systems and methods of the present invention for treating medical conditions encompass neuromodulation of any combination of one or more target sites of the sympathetic nervous system, including any combination of one or more target sites in communication with the sympathetic nerve chain. The systems and methods of the present invention also encompass ipsilateral, contralateral, and bilateral neuromodulation.

As used herein, the term "treating" a medical condition encompasses therapeutically regulating, preventing, improving, alleviating the symptoms of, reducing the effects of and/or diagnosing the medical condition. As used herein, the term "medical condition" encompasses any condition, disease, disorder, function, abnormality, or deficit influenced by the autonomic nervous system. Further, the systems and methods of the present invention can be used to treat more than one medical condition concurrently. Non-limiting examples of medical conditions that can be treated according to the present invention include genetic, skeletal, immunological, vascular or hematological, muscular or connective tissue, neurological, ocular, auditory or vestibular, dermatological, endocrinological, olfactory, cardiovascular, genitourinary, psychological, gastrointestinal, respiratory/pulmonary, neoplastic, or inflammatory medical conditions. Further, the medical condition can be the result of any etiology including vascular, ischemic, thrombotic, embolic, infectious (including bacterial, viral, parasitic, fungal, abscessal), neoplastic, drug-induced, metabolic, immunological, collagenic, traumatic, surgical, idiopathic, endocrinological, allergic, degenerative, congenital, or abnormal malformational causes.

The present invention also encompasses enhancing the therapeutic effects of other therapies, such as methods and systems working in conjunction with a pharmaceutical agent or other therapies to augment, enhance, improve, or facilitate other therapies (adjunctive therapies) as well as reducing/minimize and counteracting side effects, complications and adverse reactions for any therapies involved in treating the above-mentioned medical conditions. For example, the methods and systems of the present invention may be used for a cancer patient undergoing chemotherapy utilizing stimulation to minimize the adverse effects of chemotherapy. In contrast, the methods and systems can be used to enhance chemotherapy.

With respect to treating genetic medical conditions, such medical conditions can affect single organs, organ systems, or multiple organs in multiple organ systems.

With respect to treating skeletal medical conditions, such medical conditions can involve any medical conditions related to the components of the skeletal system such as, for example, bones, joints, or the synovium. Non-limiting examples of such skeletal medical conditions include fractures, osteoporosis, osteomalacia, osteopenia, arthritis, and bursitis.

With respect to treating immunological, inflammatory, and allergic medical conditions, such medical conditions can involve any medical conditions related to the components of the immune system such as, for example, the spleen or thymus. Non-limiting examples of immunological medical conditions include immuno-suppressed states, immuno-compromised states, auto-immune disorders, drug-related allergy, an environmental allergy, or hypogamaglobunimia.

With respect to treating vascular or hematological medical conditions, such medical conditions can involve any medical conditions related to the components of the vascular system such as, for example, the arteries; arterioles; veins; venules; capillaries; lymph nodes; blood including plasma, white blood cells, red blood cells, and platelets. Non-limiting examples of vascular/hematological medical conditions include anemia, thrombocytosis, thrombocytopenia, neutropenia, hemophilia, lymphedema, thrombosis, vasculitis, venous insufficiency, arterial dissection, peripheral edema, blood loss, vascular insufficiency, hypercoagulable states, stroke, vasospasms, and disorders of vascular tone effecting perfusion. The vasculitis may be multifocal, systemic, or limited to the central nervous system. The hypercoagulable state may be factor V deficiency or anti-thrombin deficiency, among others. The stroke may result from cerebrovascular disease and/or ischemia from decreased blood flow/oxygenation second to occlusive or thromboembolic disease. The vasospasms may be secondary to aneurismal subarachnoid hemorrhage or vasospasm secondary to other etiologies.

With respect to treating muscular/connective tissue medical conditions, such medical conditions can involve any medical conditions related to the components of the muscular/connective tissue system such as, for example, smooth or striated muscles, tendons, ligaments, cartilage, fascia, and fibrous tissue. Non-limiting examples of muscular medical conditions include myopathy, muscular dystrophy, weakness, and muscle atrophy. The muscle atrophy may be caused by degenerative muscle disease, nerve injury, disuse atrophy or stroke. Non-limiting examples of connective tissue medical conditions include scleroderma, rheumatoid arthritis, lupus, Sjogren's syndrome, fibromyalgia, myositis, myofascial pain syndrome, and collagen vascular disease. The collagen vascular disease may be lupus or rheumatoid arthritis.

With respect to treating neurological medical conditions, such medical conditions can involve any medical conditions related to the components of the nervous system such as, for example, the brain including the cerebellum, brain stem, pons, midbrain, medulla; the spinal cord; peripheral nerves;

peripheral ganglia; and nerve plexuses. Non-limiting examples of neurological conditions include Alzheimer's disease, epilepsy, multiple sclerosis, ALS, Guillan Barre, stroke, cerebral palsy, intracerebral hemorrhage, dementia, vertigo, tinnitus, diplopia, cerebral vasospasm, aneurysm, atriovenous malformation, brain malformations, Parkinson's disorder, multi-system atrophy, olivopontocerebellar degeneration, familial tremor dystonia including cervical dystonia, torticollis, facial dystonia, blepharospasms, spasmodic dysphonia, radiculopathy, neuropathy, sleep disorders, disorders of temperature regulation in the body and extremities, postherpetic neuralgia involving the face, head, body or extremities. The neuropathy may be caused by fracture, crush injury, compressive injury, repetitive movement injury, diabetes, trauma, alcohol, infection, or hereditary. The sleep disorder may be sleep apnea, restless leg syndrome, narcolepsy, snoring, insomnia, and drowsiness.

With respect to treating ocular medical conditions, such medical conditions can involve any medical conditions related to the components of the visual system such as, for example, the eye including the lens, iris, conjunctiva, lids, cornea, retina including macula, the vitreous chambers, and the aqueous chambers. Non-limiting examples of ocular medical conditions include myopia, hyperopia, exopthalmous, astigmatism, corneal ulcer, strabismus, retinitis pigmentosa, retinal tears, macular degeneration, cataracts, xerophthamia, amblyopia, and astigmatism, glaucoma, blindness, and diplopia.

With respect to treating auditory and vestibular medical conditions, such medical conditions can involve any medical conditions related to the components of the auditory and vestibular system such as, for example, the ear including the external ear, the middle ear, the inner ear, cochlea, ossicles, tympanic membrane, and semicircular canals. Non-limiting examples of auditory and vestibular medical conditions include otitis, vertigo, hearing loss, dizziness, and tinnitus.

With respect to treating dermatological medical conditions, such medical conditions can involve any medical conditions related to the components of the skin and integumentary system such as, for example, the hair, skin, nails, and sweat glands. Non-limiting examples of dermatological medical conditions include rosacea, eczema, psoriasis, acne, hair loss, hypertrichosis, seborrheic dermatitis, xerotic skin, oily skin, atrophy/dystrophy of the skin, wrinkles, radiation induced damage, vitiligo, and cellulite.

With respect to treating endocrinological medical conditions, such medical conditions can involve any medical conditions related to the components of the endocrine system such as, for example, the pancreas, thyroid, adrenal glands, liver, pituitary, and hypothalamus. Non-limiting examples of endocrinological conditions include hypoglycemia, diabetes type I and II, obesity, hyperthyroidism, hypothyroidism, amenorrhea, dysmenorrhea, infertility, impotence, anorgasmia, delayed orgasm, perimenstrual syndrome, hypercholesterolemia, hypertriglycridinemia, Cushing's disease, Addison's disease, malabsorption syndrome, dysautonomia, chronic fatigue syndrome, fatigue, heat exhaustion, cold extremities, hot flashes, vasomotor instability, Raynaud's syndrome, hormonal disorders, metabolic disorders such as gout, disorders of metabolism and metabolic storage diseases where there is an accumulation of abnormal amounts of various substances such as glycogen in glycogen storage diseases, iron in hemochromatosis or copper in Wilson's disease.

With respect to treating olfactory medical conditions, such medical conditions can involve any medical conditions related to the components of the olfactory system such as, for example, the nose, sensory nerves for smell, and sinuses. Non-limiting examples of olfactory conditions include loss of sense of smell, rhinorrhea, rhinitis, acute sinusitis, chronic sinusitis, or nasal congestion.

With respect to treating cardiovascular medical conditions, such medical conditions can involve any medical conditions related to the components of the cardiovascular system such as, for example, the heart and aorta. Non-limiting examples of cardiovascular conditions include post-infarction rehabilitation, valvular disease, myocardial infarction, arrhythmia, heart failure, angina, microvascular ischemia, myocardial contractility disorder, cardiomyopathy, hypertension, orthostatic hypotension, dysautonomia, syncope, vasovagal reflex, carotid sinus hypersensitivity, and cardiac structural abnormalities such as septal defects and wall aneurysms. The cardiomyopathy may be caused by hypertension, alcohol, or by a congenital cause. The hypertension may be essential, primary, secondary, or renal.

With respect to treating genitourinary medical conditions, such medical conditions may involve any medical conditions related to the components of the genitourinary system such as, for example, the ovary, fallopian tube, uterus, vagina, penis, testicles, kidney, bladder, ureter, and urethra. Non-limiting examples of genitourinary medical conditions include impotence, dysmenorrhea, amenorrhea, anorgasmia, delayed orgasm, endometriosis, infertility, uterine fibroids, ovarian cysts, spastic bladder, flaccid bladder, interstitial cystitis, polycystic kidney disease, nephrotic syndrome, uremia, glumerolonephritis, renal failure, urinary incontinence or hesitancy, uremia, nephrolithiasis, and benign prosthetic hyperplasia.

With respect to treating psychological medical conditions, non-limiting examples of such medical conditions include Tourette's syndrome, autism, mental retardation, stress, anxiety, depression, bipolar disorder, mania, schizophrenia, a personality disorder, a phobia, hallucinations, delusions, psychosis, addictions, and other affective disorders. The addiction may be to substances or behavior. The substance may be alcohol, cigarettes, or drugs.

With respect to treating gastrointestinal medical conditions, such medical conditions can involve any medical conditions related to the components of the gastrointestinal system such as, for example, the mouth, esophagus, stomach, small intestine, large intestine, rectum, liver, gall bladder, bile ducts, and pancreas. Non-limiting examples of gastrointestinal medical conditions include hepatic failure, hepatitis, cirrhosis, dumping syndrome, cirrhosis, gastric or duodenal ulcer, irritable bowel syndrome, colitis, diverticulosis, diverticulitis, emesis, hyper emesis gravidum, bowel incontinence, constipation, diarrhea, abdominal cramps, gastro esophageal reflux, esophageal dysmotility, gastric dysmotility, cholecystitis, gall stones, pancreatic insufficiency, gas, bloating, and gastritis.

With respect to treating respiratory/pulmonary medical conditions, such medical conditions can involve any medical conditions related to the components of the respiratory system such as, for example, the trachea, bronchus, bronchioles, alveoli, lungs, and capillaries. Non-limiting examples of respiratory medical conditions include reactive airway disease, asthma, emphysema, COPD, and silicosis.

With respect to treating neoplastic processes such processes can be primary and/or metastatic and can involve the thryoid including the medullary, the liver, the pancreas (including vipoma and insulinoma), leukemia, lymphoma and other non-solid tumors, neoplastic processes of the brain, stomach, lung, colon, esophagus, bone, skin including basal cells, squamous cells, and melanoma, the bladder, kidney, prostate, breast, ovaries, uterus, nasopharynx, and sarcoma.

With respect to treating inflammatory disorders, such inflammatory disorders include, for example, inflammatory bowel disorders such as irritable bowel syndrome and Crohn's disease; and auto-immune disorders, immune disorders and rheumatological disorders.

The present invention also provides methods of treating pain syndromes. Such pain may result from one or more medical conditions comprising: migraine headaches, including migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; reflex sympathetic dystrophy, cervicalgia; glossodynia, carotidynia; cricoidynia; otalgia due to middle ear lesion; gastric pain; sciatica; maxillary neuralgia; laryngeal pain; myalgia of neck muscles; trigeminal neuralgia; post-lumbar puncture headache; low cerebro-spinal fluid pressure headache; temporomandibular joint disorder; atypical facial pain; ciliary neuralgia; paratrigeminal neuralgia; petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia; carotidynia; Vidian neuralgia; and causalgia. To neuromodulate such pain syndromes, preferably the cervical and thoracic ganglia are stimulated.

The present invention also provides methods of treating the effects of aging, burns, trauma, transplantation, radiation damage, bioterrorism, back pain, and body pain.

FIG. 1 provides an illustration of a therapy delivery device 10, according to an embodiment of the present invention positioned at a target site in the sympathetic nervous system (which in this exemplary illustration is a ganglia of the sympathetic nerve chain). Therapy delivery device is connected via a stimulation lead/catheter 20 (in embodiments where therapy delivery device is a stimulation lead and drug port respectively) for connection to a controller (not shown). The therapy delivery device has a configuration that allows the therapy deliver device to maximize contact with and optimally deliver therapy to the target site. In embodiments where the therapy delivery device is a sympathetic ganglion, preferably the therapy delivery device has a configuration as described is PCT Application No. PCT/US03/03003 entitled "Delivery Device for Stimulating the Sympathetic Nerve Chain," which is incorporated by reference herein.

In embodiments where the therapy delivery device is a stimulation lead having a lead proximal end, a lead body, and a lead distal end, the lead distal end comprises at least one electrode. The at least one electrode can be a plurality of electrodes. The electrodes at the lead distal end can be either monopolar, bipolar, or multipolar, and can operate as a cathode or an anode. The electrode can be composed of but not limited to activated iridium, rhodium, titanium, or platinum and combinations of said materials. The electrode may be coated with a thin surface layer of iridium oxide, titanium nitride or other surface modifications to enhance electrical sensitivity. The stimulation lead can also comprise carbon, doped silicon, or silicon nitride. Each lead distal end can be provided with a biocompatible fabric "collar" or band about the electrode periphery to allow it to be more readily sutured or glued into place (for electrodes to be secured in this manner). The stimulation lead may be placed permanently or temporarily in the target site to provide chronic or acute neuromodulation of the target site.

The controller is used to operate and supply power to the therapeutic delivery device and enable the therapy delivery device to delivery a therapy signal (such as an electrical signal or a chemical signal) to the target site. The controller may be powered by a battery (which can be rechargable), an external power supply, a fuel cell, or a battery pack for external use. The controller may also be integral with the therapeutic delivery device (such as a single stimulation lead/power generator). When the therapeutic delivery device is a stimulation lead, the controller may change the output to the electrode by way of polarity, pulse width, amplitude, frequency, voltage, current, intensity, duration, wavelength, and/or waveform. When the therapeutic delivery device is a drug port, the controller may change its output such that a pump, pressure source, or proportionally controlled orifice increases or decreases the rate at which the pharmaceutical is delivered to the target site. The controller may operate any number or combination of electrodes, and pharmaceutical delivery devices, for example the controller may be connected to stimulation leads and a peristaltic pump for delivering a pharmaceutical to the target site near the stimulation leads. The controller may be implanted within the patient or it may be positioned by leads outside of the patient. A portion of the control system may be external to the patient's body for use by the attending physician to program the implanted controller and to monitor its performance. This external portion may include a programming wand which communicates with the implanted controller by means of telemetry via an internal antenna to transmit parameter values (as may be selectively changed from time to time by subsequent programming) selected at the programmer unit, such as a computer. The programming wand also accepts telemetry data from the controller to monitor the performance of the therapy delivery device.

In embodiments where the controller enables a stimulation lead to deliver an electrical signal to the target site, the electrical signal may be episodic, continuous, phasic, in clusters, intermittent, upon demand by the patient or medical personnel, or preprogrammed to respond to a sensor. Preferably, the oscillating electrical signal is operated at a voltage between about 0.1 microvolts to about 20 V. More preferably, the oscillating electrical signal is operated at a voltage between about 1 V to about 15 V. For microstimulation, it is preferable to stimulate within the range of 0.1 microvolts to about 1 V. Preferably, the electric signal source is operated at a frequency range between about 2 Hz to about 2500 Hz. More preferably, the electric signal source is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 500 microseconds. Preferably, the application of the oscillating electrical signal is: monopolar when the stimulation lead is monopolar; bipolar when the stimulation lead is bipolar; and multipolar when the stimulation lead is multipolar. The waveform may be, for example, biphasic, square wave, sine wave, or other electrically safe and feasible combinations. The electrical signal may be applied to multiple target sites simultaneously or sequentially.

In embodiments where the controller enables a drug port to deliver a chemical signal to the target site, a chemical agent may be delivered to the target site prior to, concurrent with, subsequent to or instead of electrical neuromodulation. The chemical agent may be a neurotransmitter mimick; neuropeptide; hormone; pro-hormone; antagonist, agonist, reuptake inhibitor, or degrading enzyme thereof; peptide; protein; therapeutic agent; amino acid; nucleic acid; stem cell or any combination thereof and may be delivered by a slow release matrix or drug pump. The delivery of the chemical agent may be continuous, intermittent, chronic, phasic, or episodic. Different chemical agents may be utilized to affect different parts of the sympathetic nervous system. The chemical agents preferably work on one or more of the receptor sites of the autonomic nervous system such as the adrenergic receptors, cholinergic receptors (nicotinic and muscarinic), purinergic, and nitric oxide receptors. Non-limiting examples of chemical agents include, prazosin, yohimbine, atelenol, sulbutamol, and atropine.

The present invention also provides systems for treating medical conditions incorporating a closed-loop feedback mechanism. Specifically, in such embodiments, the system comprises a therapy delivery device for applying a therapy signal (which can be an electrical signal or a chemical signal) on a target site of the sympathetic nervous system, and preferably a target site in communication with a sympathetic nerve chain. The system further comprises a sensor for detecting a bodily activity associated with the medical condition and for generating a sensor signal. The system also includes a controller in communication with the therapy delivery device for activating the therapy delivery device to initiate application of the therapy signal to the target site or to adjust application of the therapy signal to the target site in response to the sensor signal. The bodily activity to be detected by the sensor is any characteristic or function of the body, such as electrical or chemical activity and includes, for example, temperature, respiratory function, heart rate, capillary pressure, venous pressure, perfusion, oxygenation including blood oxygenation levels, oxygen saturation levels, oxygen consumption, oxygen pressure, water pressure, nitrogen pressure, carbon dioxide pressure in the tissue, circulation (including blood and lymphatic), electrolyte levels in the circulation/tissue, diffusion or metabolism of various agents and molecules (such as glucose), neurotransmitter levels, body temperature regulation, blood pressure, blood viscosity, metabolic activity, cerebral blood flow, pH levels, vital signs, galvanic skin responses, perspiration, electrocardiogram, electroencephalogram, action potential conduction, chemical production, body movement, response to external stimulation, cognitive activity, dizziness, pain, flushing, motor activity including muscle tone, visual activity, speech, balance, diaphragmatic movement, chest wall expansion, concentration of certain biological molecules/substances in the body such as, for example, glucose, liver enzymes, electrolytes, hormones, creatinine, medications, concentration of various cells, platelets, or bacteria. These bodily activities can be measured utilizing a variety of methods including but not limited to chemical analysis, mechanical measurements, laser, and fiber-optic analysis. Non-limiting examples of further tests and bodily activities that can be sensed for categories of medical conditions and specific medical conditions are provided in TABLE I. Table I is only exemplary and non-exhaustive and other bodily activities can be sensed, as well as various combinations of the sensed activities listed in Table I.

In specific embodiments, the sensors are located on or within the body and detect electrical and/or chemical activity. Such activity may be detected by sensors located within or proximal to the target site, distal to the target site but within the nervous system, or by sensors located distal to the target site outside the nervous system. Examples of electrical activity detected by sensors located within or proximal to the target site include sensors that measure neuronal electrical activity, such as the electrical activity characteristic of the signaling stages of neurons (i.e. synaptic potentials, trigger actions, action potentials, and neurotransmitter release) at the target site and by afferent and efferent pathways and sources that project to and from or communicate with the target site. For example, the sensors can measure, at any signaling stage, neuronal activity of any of the extensive connections of the target site. In particular, the sensors may detect the rate and pattern of the neuronal electrical activity to determine the electrical signal to be provided to the lead.

Examples of chemical activity detected by sensors located within or proximal to the target site include sensors that measure neuronal activity, such as the modulation of neurotransmitters, hormones, pro-hormones, neuropeptides, peptides, proteins, electrolytes, or small molecules by the target site and modulation of these substances by afferent and efferent pathways and sources that project to and from the target sites or communicate with the target sites.

With respect to detecting electrical or chemical activity of the body by sensors located distal to the target site but still within the nervous system, such sensors could be placed in the brain, the spinal cord, cranial nerves, and/or spinal nerves. Sensors placed in the brain are preferably placed in a layerwise manner. For example, a sensor could be placed on the scalp (i.e. electroencephalogram), in the subgaleal layer, on the skull, in the dura mater, in the sub dural layer and in the parenchyma (i.e. in the frontal lobe, occipital lobe, parietal lobe, temporal lobe) to achieve increasing specificity of electrical and chemical activity detection. The sensors could measure the same types of chemical and electrical activity as the sensors placed within or proximal to the target site as described above.

With respect to detecting electrical or chemical activity by sensors located distal to the target site outside the nervous system, such sensors may be placed in venous structures and various organs or tissues of other body systems, such as the endocrine system, muscular system, respiratory system, circulatory system, urinary system, integumentary system, and digestive system or such sensors may detect signals from these various body systems. For example, the sensor may be an external sensor such as a pulse oximeter, or an external blood pressure, heart, and respiratory rate detector. All the above-mentioned sensing systems may be employed together or any combination of less than all sensors may be employed together.

After the sensor(s) detect the relevant bodily activity associated with the medical condition, according to the systems of the present invention, the sensors generate a sensor signal. The sensor signal is processed by a sensor signal processor, which in this embodiment is part of the controller. The controller generates a response to the sensor signal by activating the therapy delivery device to initiate application of the therapy signal or to adjust application of the therapy signal to the target site. The therapy deliver device then applies the therapy signal to the target site. In embodiments where the therapy delivery device is a stimulation lead and the therapy signal is an electrical signal, activating the stimulation lead to adjust application of the electrical signal includes terminating, increasing, decreasing or changing the rate or pattern of a pulsing parameter of the electrical stimulation and the electrical signal can be the respective termination, increase, decrease or change in rate or pattern of the respective pulsing parameter. In embodiments where the therapy delivery device is a drug port and the therapy signal is a chemical signal, activating the drug port to adjust application of the chemical signal can be an indication to terminate, increase, decrease or change the rate or pattern of the amount or type of chemical agent administered, and the chemical signal can be the respective initiation, termination, increase, decrease or change in the rate or pattern of the amount or type of chemical agent administered. The processing of closed-loop feedback systems for electrical and chemical stimulation are described in more detail in respective U.S. Pat. Nos. 6,058,331 and 5,711,316, both of which are incorporated by reference herein.

Figure 2:
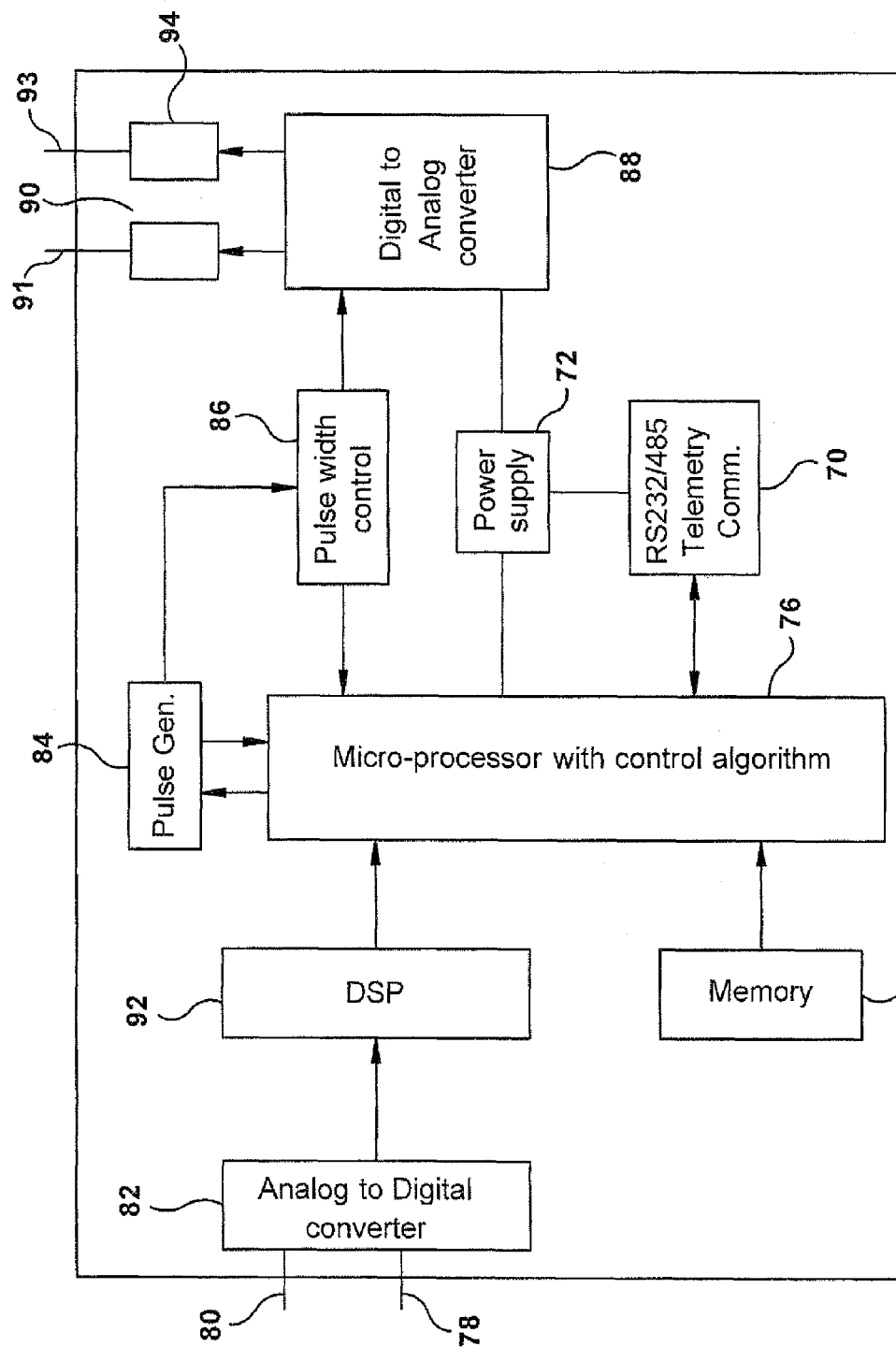
FIG. 2 is a schematic illustration of the components which may be used in a controller of the present invention.

Closed-loop electrical stimulation, according to the present invention can be achieved by a modified form of an implantable SOLETRA, KINETRA, RESTORE, or SYNERGY signal generator available from Medtronic, Minneapolis, Minn. as disclosed in U.S. Pat. No. 6,353,762, the teaching of which is incorporated herein in its entirety, a controller as described in FIG. 2, or utilization of CIO DAS 08 and CIO-DAC 16 I processing boards and an IBM compatible computer available from Measurement Computing, Middleboro, Mass. with Visual Basic software for programming of alogorithms. With reference to FIG. 2 an illustration of a non-limiting example of a controller comprising a microprocessor 76 such as an MSP430 microprocessor from Texas Instruments Technology, analog to digital converter 82 such as AD7714 from Analog Devices Corp., pulse generator 84 such as CD1877 from Harris Corporation, pulse width control 86, lead driver 90, digital to analog converter 88 such as MAX538 from Maxim Corporation, power supply 72, memory 74, and communications port or telemetry chip 70 are shown. Optionally, a digital signal processor 92 is used for signal conditioning and filtering. Input leads 78 and 80 and output lead to lead (therapeutic delivery device) 91 and drug delivery device (therapeutic deliver device) 93 are also illustrated. Additional stimulation leads, sensors, and therapeutic delivery devices may be added to the controller as required. As a non-limiting example, inputs from sensors, such as heart rate and blood pressure sensors, are input to analog to digital converter 82. Microprocessor 76 receiving the sensor inputs uses algorithms to analyze the biological activity of the patient and using HD, Fuzzy logic, or other algorithms, computes an output to pulse generator and/or drug delivery device drivers 90 and 94, respectively, to neuromodulate the target site where the therapeutic delivery devices are placed. The output of analog to digital converter 82 is connected to microprocessor 76 through a peripheral bus including address, data and control lines. Microprocessor 76 processes the sensor data in different ways depending on the type of transducer in use. When the signal on the sensor indicates biological activity outside of threshold values, for example elevated blood pressure or heart rate, programmed by the clinician and stored in a memory, the electrical signal applied through output drivers 90 and 94 of the controller will be adjusted. The output voltage or current from the controller are then generated in an appropriately configured form (voltage, current, frequency), and applied to the one or more therapeutic delivery devices placed at the target site for a prescribed time period to reduce elevated blood pressure or heart rate. If the patient's blood pressure or heart rate as monitored by the system is not outside of the normal threshold limits (hypotensive or hypertensive, bradycardic or tachycardic), or if the controller output (after it has timed out) has resulted in a correction of the blood pressure or heart rate to within a predetermined threshold range, no further electrical signal is applied to the target site and the controller continues to monitor the patient via the sensors. A block diagram of an algorithm which may be used in the present invention is shown in FIG. 3.

Figure 3:
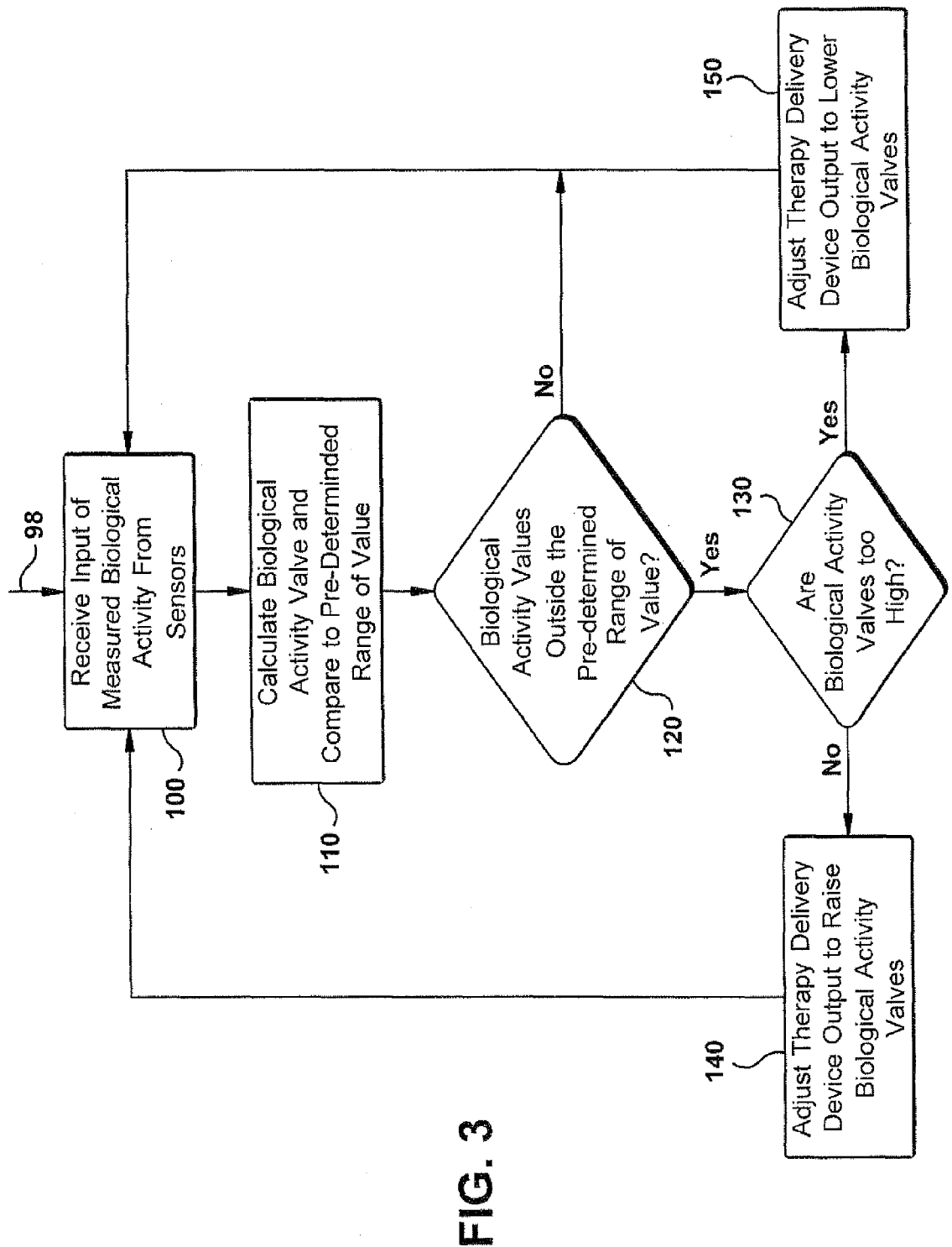
FIG. 3 is a block diagram of an algorithm to determine action which may be taken by the controller microprocessor in response to sensor input.

Referring to FIG. 3, suitably conditioned and converted sensor data 98 is input to the algorithm in block 100. The program computes at least one value of at least one biological activity related to a particular medical condition such as, for example, blood pressure, heart rate, or cardiac output, and compares the measured value of the biological activity to a pre-determined range of values, which is determined in advance to be the desired therapeutic range of values. This range is programmed into the microprocessor via the telemetry or communications port of the controller. The algorithm compares, 110, and then determines whether or not the measured value lies outside the pre-determined range of values, 120. If the measured biological activity value is not outside the pre-determined range of values, the program continues to monitor the sensors and reiterates the comparison part of the algorithm. If the measured biological value is outside of the pre-determined range of values, a determination or comparison is made, 130, as to whether the value is too high or too low compared with the pre-determined range. If the biological activity value is too high, an adjustment to the therapeutic delivery device is made, 150, to lower the biological activity value of the patient by calculating an output signal for pulse generator or drug delivery device to deliver a sufficient amount of the pharmaceutical or electrical stimulation to lower the biological activity of the patient. The algorithm continues to monitor the biological activity following the adjustment. If the biological activity value is too low then an adjustment to the therapeutic delivery device is made, 140, to raise the biological activity value by calculating an output signal for the pulse generator or drug delivery device to deliver a sufficient amount of a pharmaceutical or electrical stimulation to raise the biological activity value of the patient. The algorithm continues to monitor the biological activity of the patient, 100, following the adjustment. The amount of adjustment made may be determined by proportional integral derivative algorithms of by implementation of Fuzzy logic rules.

With respect to the control of specific electrical parameters, the stimulus pulse frequency may be controlled by programming a value to a programmable frequency generator using the bus of the controller. The programmable frequency generator provides an interrupt signal to the microprocessor through an interrupt line when each stimulus pulse is to be generated. The frequency generator may be implemented by model CDP1878 sold by Harris Corporation. The amplitude for each stimulus pulse may be programmed to a digital to analog converter using the controller's bus. The analog output is conveyed through a conductor to an output driver circuit to control stimulus amplitude. The microprocessor of the controller may also program a pulse width control module using the bus. The pulse width control provides an enabling pulse of duration equal to the pulse width via a conductor. Pulses with the selected characteristics are then delivered from signal generator through a cable and lead to the target site or to a device such as a proportional valve or pump. For some types of sensors, a microprocessor and analog to digital converter will not be necessary. The output from sensor can be filtered by an appropriate electronic filter in order to provide a control signal for signal generator. An example of such a filter is found in U.S. Pat. No. 5,259,387 Muscle Artifact Filter, Issued to Victor de Pinto on Nov. 9, 1993, incorporated herein by reference in its entirety.

At the time the therapy delivery device is implanted, the clinician programs certain key parameters into the memory of the implanted device via telemetry. These parameters may be updated subsequently as needed. The clinician may also program the the range of values for pulse width, amplitude and frequency which the therapy delivery device may use to optimize the therapy. The clinician may also choose the order in which the parameter changes are made. Alternatively, the clinician may elect to use default values or the microprocessor may be programmed to use fuzzy logic rules and algorithms to determine output from the therapeutic delivery device to the patient based on sensor data and threshold values for the biological activity.

Although the application of sensors to detect bodily activity are part of embodiments of systems of the present invention, the present invention also contemplates the relevant bodily activity to be detected without sensors. In such case, the neuromodulation parameters are adjusted manually in response to the clinical course of the disease or reporting by the patient.

In another embodiment, the present invention provides a method of stabilizing and/or optimizing bodily functions, augmenting function and treating the various diseases/disorders listed in Table I by placing a therapy delivery device on a target site of the sympathetic nervous system, and preferably a target site in communication with a sympathetic nerve chain, and activating the therapy delivery device to apply a therapy signal (electrical and/or chemical signal) to the target site to stabilize and/or optimize the bodily function as well as to enhance, augment, normalize, regulate, control and/or improve the normal and abnormal functioning of the various body organs/structures/systems (for example heart, lung, gastrointestinal, genitourinary, vascular, and other systems) that are innervated by the sympathetic nervous system. This method can be performed in the operating room, procedure room or imaging (MRI, CT, X-ray, fluoroscopy or optical imaged guided) suite. The procedures can be carried out peri-operative or post-operative to a surgical operation as well as in an intensive care unit and any other commonly utilized in-patient and out-patient capacities. Preferably, the surgical operation includes procedures that may require heart bypass equipment, procedures that may require a respiratory ventilator, or surgeries where intravenous medications are used during and after surgery to influence cardiac and/or pulmonary function. In an alternative embodiment, this method is performed in a non-surgical setting where intravenous medications are used for sedation, analgesia and to stabilize cardiac function, such as in the setting of myocardial infarction.

The present invention also provides a method for minimizing or resolving side effects and morbidity associated with other therapies used for various disorders including medications, surgery, chemotherapy, and radiation.

Neuromodulation of the target sites of the present invention can be temporary or short term, such as less than 10 days, intermediate (10-30 days) or chronic (greater than 30 days). Further, the target sites can be accessed using any of the current approaches used by neurosurgeons, spinal surgeons, cardio-thoracic surgeons, vascular surgeons, abdominal surgeons, GU surgeons, ENT surgeons, plastic surgeons as well as interventional radiologists, neurologists, pain management specialists, rehabilitation and physical therapy specialists and anesthesiologists. The procedures involves direct and indirect placement of the therapy delivery device. This can be achieved using percutaneous, endoscopic, intravascular, or open surgical approach. Furthermore all these approaches can be guided by imaging means of MRI/CT/X-ray/fluoroscopy/optical imaging. A variety of approaches are available and practiced routinely by the group of specialists listed above. Non-limiting and commonly employed procedures are posterior paravertebral thoracic sympathectomy, thoracoscopic sympathectomy, and retroperitoneal lumbar sympathectomy. Reference is made to "Surgical Management of Pain", Thieme Medical Publishers, Inc. RD 595.5.587 (2001) incorporated in its entirety herein by reference thereto for further details. For open surgery, anterior supraclavicular, transaxillary, and posterior paravertebral approaches can be used.

Figure 4:
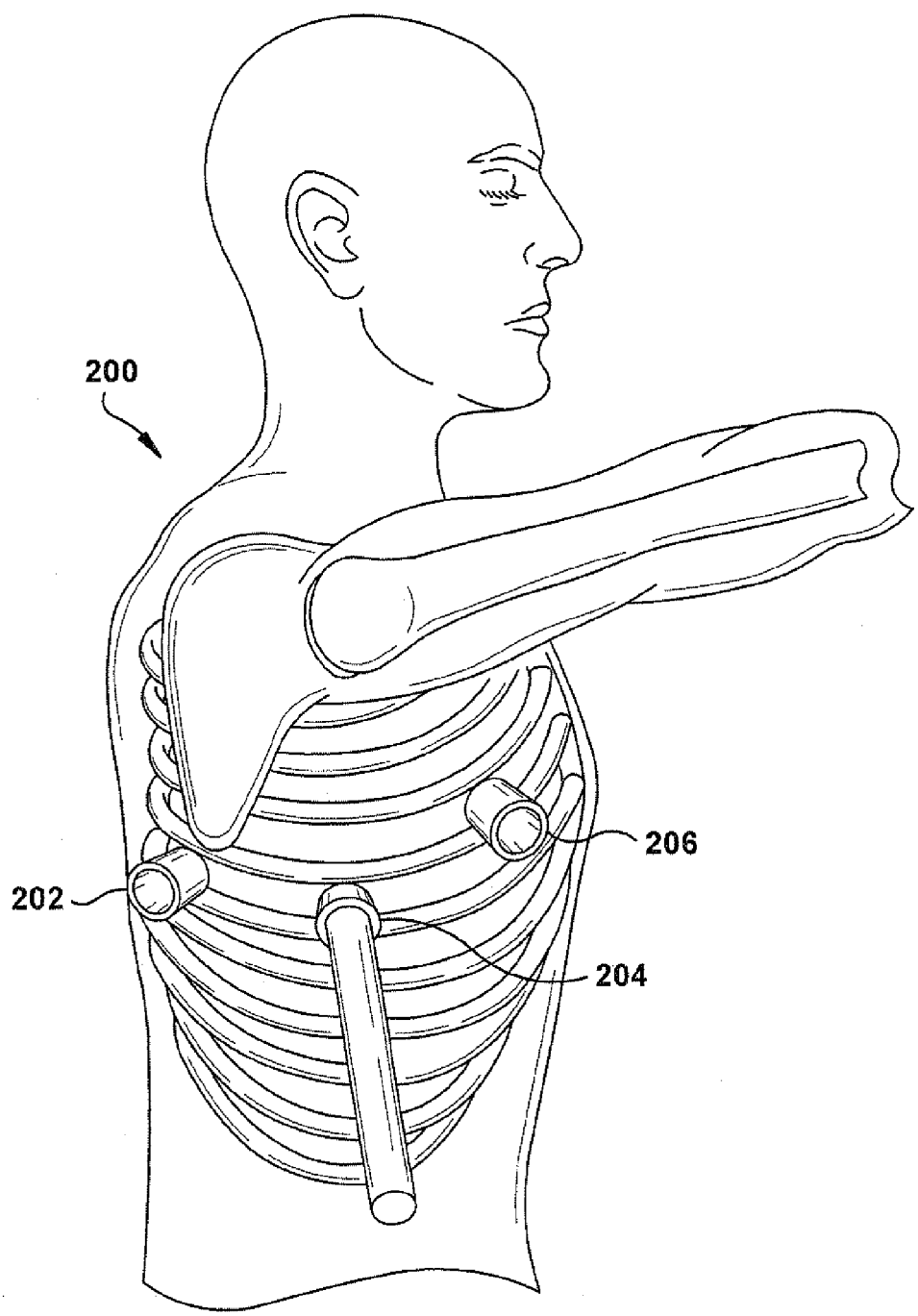
FIG. 4 is a schematic illustration of a patient lying in the lateral decubitus position having one visualization port in the fifth intercostal space at the mid-axillary line and two instrument ports at the fourth and fifth intercostal space at the anterior and posterior axillary lines, respectively.

A non-limiting example of a method of placing a therapy delivery device on a target site of the sympathetic nervous system will now be described. Referring to FIG. 4, a patient 200 is illustrated in the decubitus position where the hips of the patient 200 are preferably below the flexion joint of the operating room table. Subsequent flexion of the table allows some separation of the ribs by dropping the patient's hips and therefore increasing the intercostal space to work through. The ipsilateral arm is abducted on an arm holder. Rotating the table somewhat anteriorly and using reverse Trendelenburg positioning further maximizes the exposure to the superior paravertebral area by allowing the soon to be deflated lung (see FIGS. 5 and 6) to fall away from the apical posterior chest wall. This is the preferred position of the patient 200 prior to performing the procedure as this position exposes the vertebral bodies where the sympathetic nerve chain lies extrapleurally.

The procedure begins with placing the patient 200 under general anesthesia and intubated via a double lumen endotracheal tube. The double lumen endotracheal tube permits ventilation of one lung and collapse of the other lung that is to be operated upon without using carbon dioxide insufflation. One incision is made in the midaxillary line in the fifth intercostal space that is identified as port 204. Port 204 can be used for various reasons, but it is preferred that port 204 is used as a telescopic video port which will provide video assistance during the procedure. While under endoscopic observation, a second incision is made in the third or fourth intercostal space at the anterior axillary line that is identified as port 206. Port 206 is preferably used as an instrument channel. A third incision is made at the posterior axillary line just below the scapular tip in the fifth interspace that is identified as port 202. Port 206 is preferably used as a second instrument channel. Preferably, the three incisions made during the thoracoscopic sympathectomy are approximately 2 cm in length. Additional incisions (i.e., ports) can be made as necessary.

Figure 5:
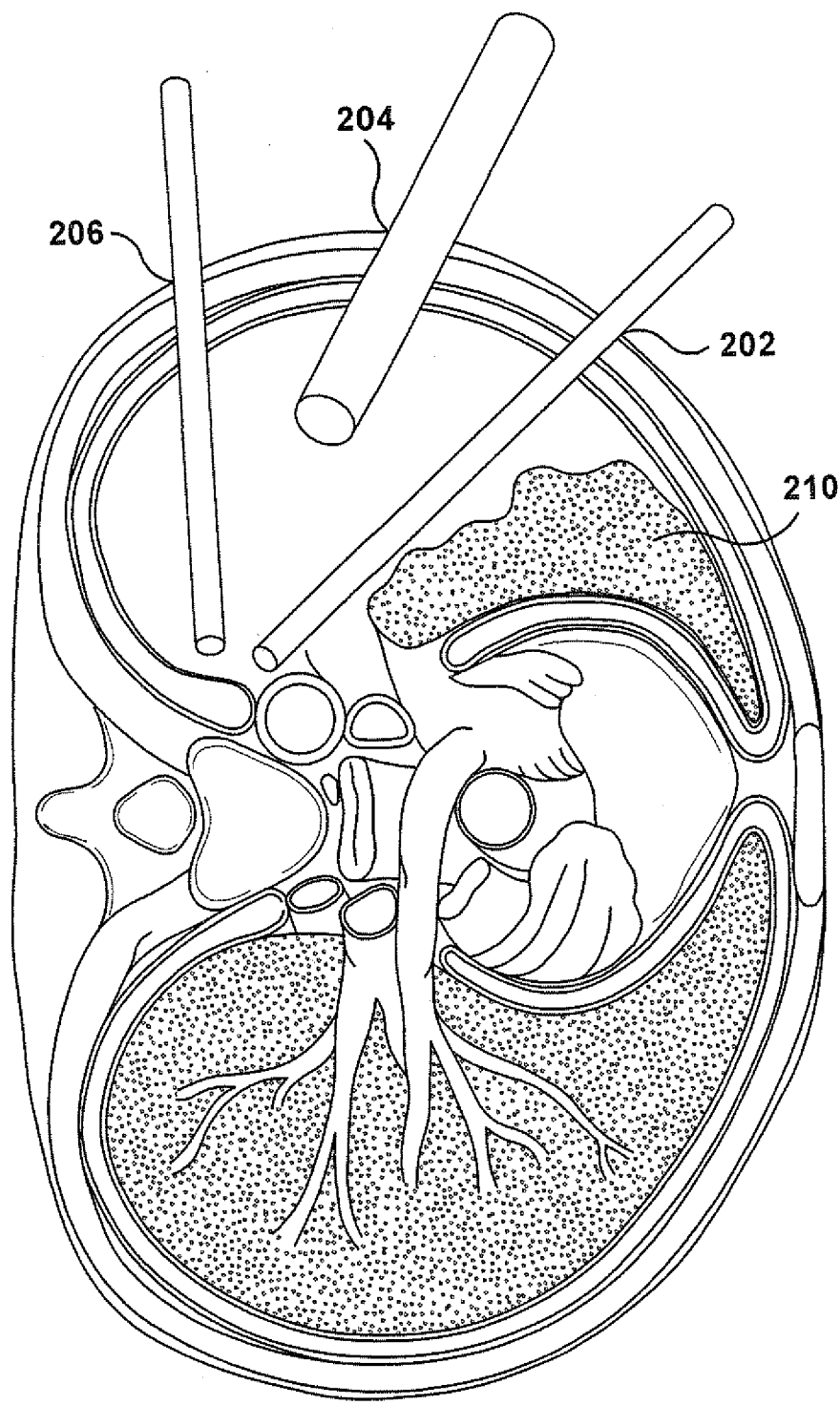
FIG. 5 is an axial cross section view of the upper thoracic region including one visualization port and two instrument ports wherein the two instrument ports have disposed therethrough endoscopic instruments accessing the ipsilateral paravertebral region where the sympathetic nerve chain lies.
Figure 6:
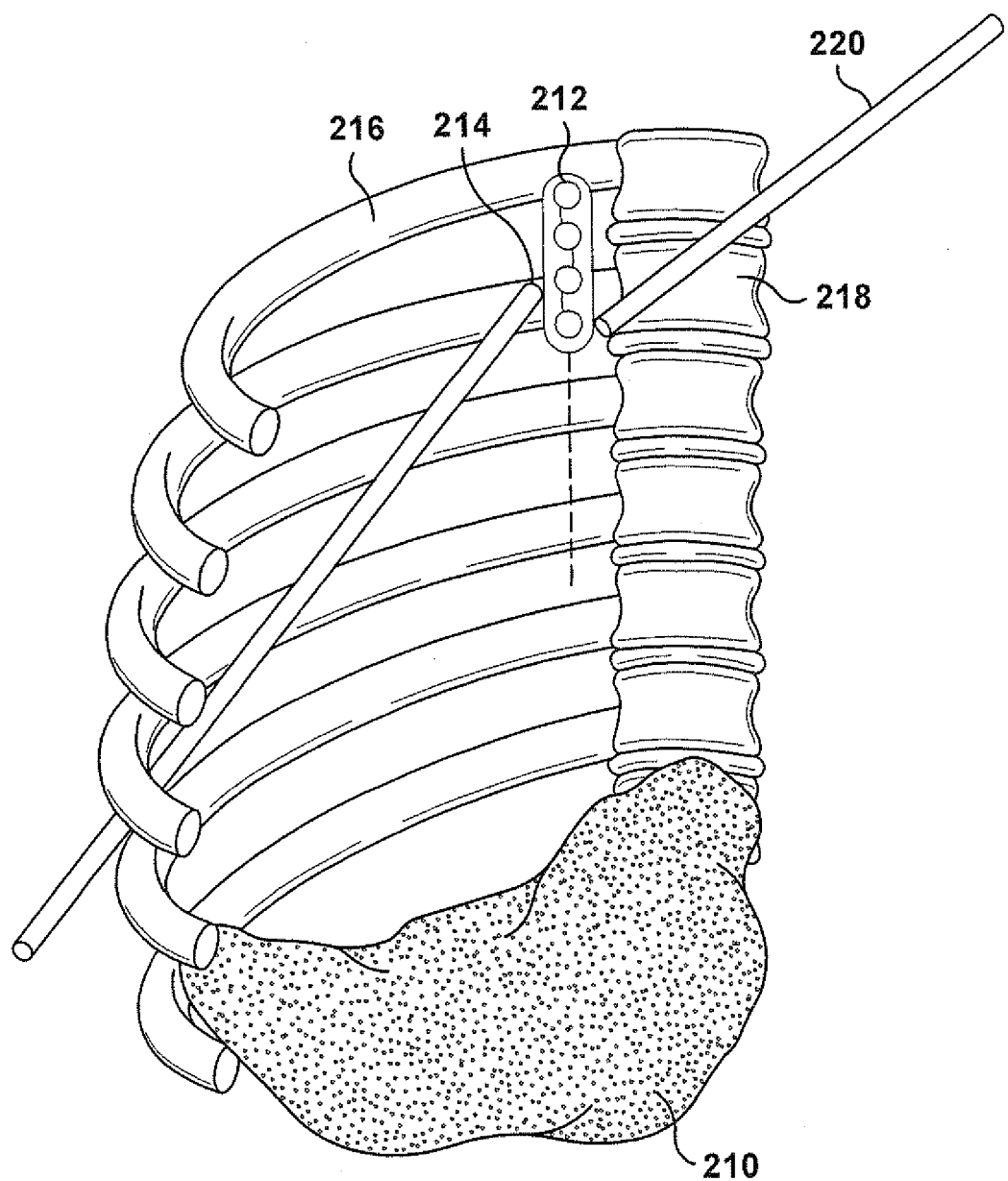
FIG. 6 is an exposed view of the left hemithorax displaying one instrument tenting the parietal pleura while the second endoscopic instrument is incising the parietal pleura to expose the sympathetic nerve chain.

Referring to FIGS. 5 and 6, in which axial cross section and exposed views of the surgical sites are provided, respectively, the surgical exposure and preparation of the relevant portion of the sympathetic nerve chain for the treatment of various physiological and pathological conditions is described. After the lung 210 is collapsed, and if necessary, retracted down by a fanning instrument via one of the working ports, the sympathetic nerve chain 212 is visualized under the parietal pleura 214 as a raised longitudinal structure located at the junction of the ribs 216 and the vertebral bodies 218. The parietal pleura 214 is grasped between the first and second ribs in the region overlying the sympathetic nerve chain 212 and scissors 220 or endoscopic cautery is used to incise the parietal pleura 214 in a vertical manner just below the first rib thereby exposing the sympathetic nerve chain 212.

Figure 7:
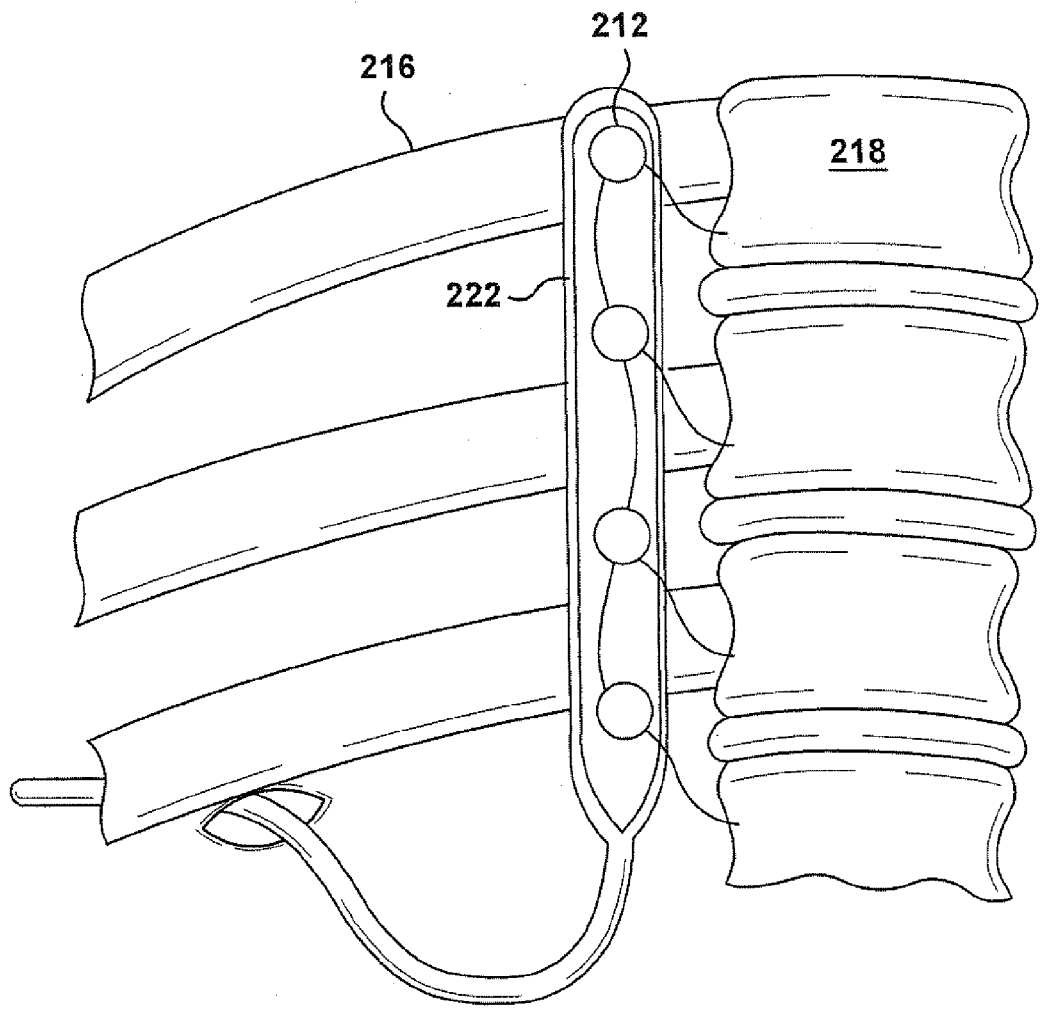
FIG. 7 is a side view of an exposed superior thoracic ganglia in which a therapy delivery device is disposed adjacent thereto.

Referring now to FIG. 7, in which the implantation of a multichannel stimulation lead 222 at a specific location of the sympathetic nerve chain is shown, the implantation of the stimulation lead 222 is now described. Once the sympathetic nerve chain 212 has been exposed, a multichannel stimulation lead 222 is implanted adjacent to a predetermined site along the sympathetic nerve chain that is associated with the physiological disorder or pathological condition being treated. The stimulation lead 222 is sutured in place to the nearby tissue or parietal pleura 214. The vicinity of the sympathetic nerve chain for which the stimulation lead is positioned depends on the physiological disorder or pathological condition being treated.

The influence of the neuromodulation of the systems and methods of the present invention can be manifested as changes in biological activity. For example with respect to treating cardiovascular medical conditions, such changes include changes in heart rate, heart rhythm, blood flow to the heart and cardiac contractility. These changes are reflected physiologically by parameters such as, for example, heart rate, blood pressure, cardiac output, stroke volume, pulmonary wedge pressure, and venous pressure, all of which can be measured. Preferably, the neuromodulation allows for selective changes in one or more aspects of the target organ whose function is being influenced without influencing or minimally influencing other functions of the target organ. For example, cardiac function may be selectively influenced by varying the parameters of stimulation such that cardiac contractility is affected but not heart rate.

The influence of neuromodulation of this method of the present invention on the respiratory system, for example, can be manifested in respiratory rate, changes in elasticity of the lung tissue, changes in diameter of the bronchioles and other structures in the respiratory branches, perfusion and diffusion of blood and its products at the level of the alveoli and blood flow to the lungs. These changes are reflected physiologically by parameters such as, for example, respiratory rate, pH of blood, bicarbonate level, ventilatory volume, lung capacity, and blood oxygenation.

The foregoing description has been set forth merely to illustrate the invention and isnot intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. For example, although methods of treating specific medical conditions are described with respect to electrical and chemical neuromodulation, other modes of neuromodulation can be used such as light, magnetism, sound, pressure, and heat/cold. Furthermore, all references cited herein are incorporated by reference in their entirety.

TABLE I

| TYPE OF DISORDER/MEDICAL CONDITION | TYPE OF SENSING PERFORMED |
|---|---|
| SKELETAL DISORDERS | |
| osteomalacia | Radiographic, magnetic resonance imaging, computer tomography, bone densitometry, presence of effusion in joints or surrounding tissue, protein concentration and/or content in the joint or surrounding tissue, autoantibodies, antinuclear antibody, antibodies to double-stranded DNA, depressed serum complement, rheumatoid factor, creatine kinase, antinuclear antibodies, erythrocyte sedimentation rate C-reactive protein, uric acid |
| arthritis | |
| fractures | |
| osteoporosis | |
| osteopenia | |
| osteonecrosis | |
| infectious arthritis | |
| Tenosynovitis | |
| Bursitis | |
| CONNECTIVE TISSUE/RHEUMATOLOGICAL DISORDERS | |
| rheumatoid arthritis | Radiographic, magnetic resonance imaging, computer tomography, bone densitometry, presence of effusion in joints or surrounding tissue, protein concentration and/or content in the joint or surrounding tissue, autoantibodies, antinuclear antibody, antibodies to double-stranded DNA, depressed serum complement, rheumatoid factor, creatine kinase, antinuclear antibodies, erythrocyte sedimentation rate C-reactive protein, uric acid, venous pressure, Temperature, blood pressure, heart rate, pH of blood, blood oxygenation level, oxygen saturation level, blood viscosity |
| polymyositis/dermatomyositis | |
| scleroderma | |
| gout | |
| rheumatic fever | |
| Reiter's syndrome | |
| systemic lupus erythematosus | |
| myalgias/myopathy | |
| vasculitis syndrome | |
| Sjögren's syndrome | |
| rhabdomyolysis | |
| seronegative spondyloarthropathies | |
| Polymyalgia Rheumatica | |

TABLE I-continued

| TYPE OF DISORDER/MEDICAL CONDITION | TYPE OF SENSING PERFORMED |
|---|---|
| VASCULAR DISORDERS | |
| arterial aneurysms | Ultrasonography, echocardiogram, angiography, skin color, temperature, pain, neurological manifestation, presence and degree of edema, blood pressure, heart rate, urinary output, oxygen pressure in blood and/or tissues, venous pressure, temperature, blood pressure, heart rate, pH of blood, blood oxygenation level, oxygen saturation level, blood viscosity |
| aortic dissection | |
| venous occlusive disease | |
| Buerger's disease | |
| Arteritis obliterans | |
| arterial occlusive disease | |
| Takayasu's disease | |
| fibromuscular dysplasia | |
| Raynaud's syndrome | |
| livedo reticularis | |
| acrocyanosis | |
| erythromelalgia | |
| acute deep venous thrombosis | |
| Deep venous thrombosis | |
| chronic venous insufficiency | |
| lymphangitis and lymphadenitis | |
| lymphedema | |
| Thrombocytosis | |
| Thrombocytopenia | |
| Thrombosis | |
| Arterial Dissection | |
| Peripheral edema | |
| Blood Loss | |
| Vascular insufficiency | |
| hypercoagulable states | |
| hypotension and shock | |
| HEMATOLOGICAL DISORDERS | Hematocrit, neutrophil count, white count, platelet count, red cell morphology, LDH, bleeding time, factor VIII antigen, factor VIII coagulant activity, platelet function, prothrombin time, partial thromboplastin time, prothrombin time-international normalized ratio, bleeding time, factor IX levels fibrin degradation products, and prothrombin time, venous pressure, temperature, blood pressure, heart rate, pH of blood, blood oxygenation level, oxygen saturation level, blood viscosity |
| neutropenia | |
| leukemias and other myeloproliferative disorders | |
| lymphomas | |
| idiopathic thrombocytopenic purpura | |
| heparin-induced thrombocytopenia | |
| thrombotic thrombocytopenic purpura | |
| von Willebrand's disease | |
| disorders intrinsic to the platelets | |
| uremia | |
| myeloproliferative disorders | |
| hemophilia A | |
| hemophilia B | |
| syndrome of disseminated intravascular coagulation | |
| hemolytic transfusion reactions | |
| Sickle Cell Anemia | |
| anemia | |
| Hodgkin's disease | |
| ALLERGIC DISORDERS | specific-IgE antibody to tested aeroallergens, serum tryptase, immune complexes in serum or deposited in affected tissues, venous pressure, Temperature, antibody levels of immunoglobulin(Ig) M, IgG, IgA, blood pressure, heart rate, pH of blood, blood oxygenation level, oxygen saturation level, blood viscosity |

TABLE I-continued

| TYPE OF DISORDER/MEDICAL CONDITION | TYPE OF SENSING PERFORMED |
|---|---|
| Environmental Allergy | |
| Hypogamaglobunimia | |
| angioedema | |
| urticaria | |
| allergic rhinitis | |
| anaphylaxis | |
| drug allergy | |
| serum sickness | |
| amyloidosis | |
| NEUROLOGICAL DISORDERS | clinical symptons and neurological exam, subdural electrodes over the brain and/or brainstem and/or spinal cord to measure electrical activity of the brain and/or spinal cord and/or brain stem, cerebrospinal fluid (CSF) pressure, cerebrospinal fluid protein and/or glucose and/or cell count, electroencephalogram, neuronal electrical activity, transcranial magnetic stimulation, myelin basic protein in cerebrospinal fluid, cerebrospinal fluid production rate, somatosensory and/or visual and/or auditory evoked potential, single fiber electromyography, surface electromyography of the muscle tissue skin, skin temperature, heart rate, sweating, intestinal motility, sphincter control, sexual function, respiratory rate, flicker pupilary response, oximetry, transcranial Doppler, accelerometer, acetylcholine antibodies in blood |
| Alzheimers disease | |
| cerebral Palsy | |
| Intracerebral hemorrhage | |
| Diplopia | |
| Cerebral Vasospasm | |
| Amyotrophic lateral sclerosis | |
| Multiple sclerosis | |
| Aneurysm | |
| Atriovenous Malformation | |
| Brain Malformations | |
| Multi-system atrophy | |
| Olivopontocerebellar | |
| Dystonia | |
| Torticollis | |
| Blepharospasms | |
| Spasmodic dyshponia | |
| Radiculopathy | |
| Neuropathy | |
| postherpetic neuralgia on the head, body, trunk, chest or extremities | |
| epilepsy | |
| dysautonomia | |
| restless leg syndrome | |
| Carpal tunnel syndrome | |
| Tarsal tunnel syndrome | |
| epicondylitis | |
| Subclavian steel syndrome | |
| Isolated central nervous system vasculitis | |
| Systemic vasculitis | |
| Encephalitis from various causes including but not limited to Neoplastic, auto immune, infectious, etc. | |
| Meningitis including but not limited to infectious, chemical, Neoplastic, drug induced | |
| arachnoiditis | |
| cerebritis | |
| sensory disturbances in any combination (allodynia, paresthesia dysesthesia, anesthesia) | |
| Sensory loss in any combination (vibration, proprioception, temperature, light touch, pain) | |
| weakness and paralysis | |
| stroke | |
| subarachnoid hemorrhage | |
| benign essential (familial) tremor | |
| Parkinsonism | |
| Huntington's disease | |

TABLE I-continued

| TYPE OF DISORDER/MEDICAL CONDITION | TYPE OF SENSING PERFORMED |
|---|---|
| dementia | |
| multiple sclerosis | |
| stupor and coma | |
| spinal trauma | |
| motor neuron diseases | |
| Acute Idiopathic Polyneuropathy (Guillain-Barré Syndrome) | |
| Myasthenia Gravis | |
| Myasthenic Syndrome (Lambert-Eaton Syndrome) | |
| Autism | |
| hydrocephalus | |
| neuropathy | |
| Sleep apnea | |
| insomnia | |
| Snoring | |
| EAR, NOSE and THROAT DISORDERS | clinical examination audiology, caloric stimulation, electronystagmography, Radiographic, magnetic resonance imaging, computer tomography, brain stem auditory evoked potential studies, test olfaction |
| Dizziness | |
| Loss of sense of smell | |
| rhinorrhea | |
| nasal congestion | |
| hearing loss | |
| external otitis | |
| auditory tube dysfunction | |
| acute otitis media | |
| tinnitus | |
| vertigo | |
| vestibular schwannoma (Acoustic Neuroma) | |
| acute sinusitis involving one or more sinuses including sphenoid, maxillary, ethmoid, frontal | |
| olfactory dysfunction | |
| epistaxis | |
| glossitis | |
| glossodynia | |
| burning mouth syndrome | |
| dysgeusia | |
| pharyngitis and tonsillitis | |
| epiglottitis | |
| Ménière's disease | |
| Chronic Sinusitis | |
| Deviated nasal septum | |
| Intranasal polyps | |
| RESPIRATORY DISORDERS | Spirometry, measurement of air movement throughout the respiratory tree via external or internal place sensors to measure forced vital lung capacity, total lung capacity, forced expiratory lung volume, residual lung volume before and/or after the administration of a short-acting bronchodilator, Peak expiratory flow meters, arterial blood gas, D-dimer, venous pressure, Temperature, blood pressure, heart rate, pH of blood, blood oxygenation level, oxygen saturation level, blood viscosity,, diaphragmatic movement, chest wall expansion measured by a strain gauge |
| asthma | |
| chronic obstructive pulmonary disease (COPD) | |
| cystic fibrosis | |
| bronchiolitis | |
| pneumonia | |
| pulmonary thromboembolism | |
| Bronchitis | |
| Emphysema | |
| Adult respiratory distress syndrome | |
| Allergies | |
| Brochiectasis | |
| Bronchopulmonary dysplasia | |
| Chlamydia pneumoniae | |
| Chronic Bronchitis | |
| Chronic lower respiratory diseases | |
| Croup | |
| Familial emphysema | |
| High altitude pulmonary edema | |
| Idiopathic Pulmonary Fibrosis | |
| Interstitial lung disease | |

TABLE I-continued

| TYPE OF DISORDER/MEDICAL CONDITION | TYPE OF SENSING PERFORMED |
|---|---|
| Lymphangioleiomyomatosis | |
| Neonatal Respiratory Distress Syndrome | |
| Parainfluenza | |
| Pleural effusion | |
| Pleurisy | |
| Pneumothorax | |
| Primary pulmonary hypertension | |
| Psittacosis | |
| Pulmonary edema | |
| Pulmonary embolism | |
| Pulmonary hypertension | |
| Q fever | |
| Respiratory failure | |
| Respiratory syncytial virus | |
| Sarcoidosis | |
| SARS | |
| Smoking | |
| Stridor | |
| Tuberculosis | |
| acute respiratory distress syndrome (ARDS) | |
| CARDIAC DISORDERS | Echocardiogram, blood pressure, heart rate, stroke volume, electrocardiogram, coronary angiogram, angioscopy, cardiac contractility measured by myography, cardiac biopsy, pulmonary wedge pressure, venous pressure, Temperature, blood pressure, heart rate, pH of blood, blood oxygenation level, oxygen saturation level, blood viscosity, |
| congenital heart disease | |
| valvular heart disease including stenotic and/or insufficency | |
| atherosclerotic coronary artery disease | |
| Arrhythmias including but not limited to atrial fibrillation, ventricular | |
| Fibrillation, atrial flutter, ventricular flutter, tachycardia, bradycardia | |
| Tachy-brady syndrome, skipped beats, first degree heart block, | |
| Second degree heart block, atriovenous node block | |
| infectious myocarditis | |
| Ischemic heart disease | |
| Heart murmurs | |
| Rheumatic heart disease | |
| Hypertensive heart disease | |
| Ischemic stroke | |
| Hemorrhagic stroke | |
| Cortical stroke | |
| Sub cortical stroke | |
| Cerebral anoxia | |
| Cerebellar stroke | |
| Brain stem stroke. | |
| Atherosclerosis | |
| Angina | |
| Cerebral Arteriosclerosis | |
| Autoimmune Atherosclerosis | |
| Peripheral arterial disease | |
| Hypertension | |
| Heart failure right and/or left | |
| Atrial septal defect | |
| Ventricular septal defect | |
| Arterial dissection in the carorid and/or basilar and/or vertebral | |
| And/or aorta and/or renal arteries | |
| Septal aneurysm | |
| Microvascular ischemia | |
| GASTROINTESTINAL DISORDERS | |
| esophageal dysphagia | esophageal manometry, barium esophagogram, esophagography, endoscopy, receptor scintigraphy (SRS) and endoscopic ultrasonography, endoscopic mucosal biopsy, Plain film radiography, comuter tomography, colonoscopy, measurement of the surface and/or deep muscle tone of esophagus, stomach, large and small intestine, colon, rectum, measurement of discharges of nerve plexus (myenteric) in the muscle wall of colon, intestine, stomach pH, peristaltic wave measurement |

TABLE I-continued

| TYPE OF DISORDER/MEDICAL CONDITION | TYPE OF SENSING PERFORMED |
|---|---|
| | including frequency and duration, small bowel manometry, serum lipase, serum amylase, gastrin level, pepsin, chloride level, vasoactive intestinal peptide level |
| esophageal diverticula | |
| esophageal motility disorders | |
| Zollinger-Ellison syndrome | |
| celiac disease | |
| intestinal motility disorders | |
| gastroparesis chronic intestinal pseudo-obstruction | |
| irritable bowel syndrome | |
| colonic diverticulosis | |
| Chronic digestive diseases | |
| inflammatory bowel disease | |
| Crohn's disease | |
| ulcerative colitis | |
| gastroparesis | |
| diabetic gastroparesis | |
| diabetic diarrhea | |
| Celiac disease | |
| Lactose Intolerance | |
| Cystic Fibrosis | |
| Esophagitis | |
| Gastroesophageal reflux disease | |
| Gastritis | |
| Diarrhea | |
| Abdominal cramps | |
| constipation | |
| cholecystitis | |
| Biliary stasis | |
| Ascites | |
| Hepatic failure | |
| Cirrhosis | |
| Hepatic encephalopathy | |
| Hepatitis acute and/or chronic | |
| gastroenteritis | |
| Achalasia | |
| gas | |
| Acute Nonulcer dyspepsia | |
| Acute Pancreatitis | |
| Amebic dysentery | |
| Anthrax | |
| Bacterial digestive infections | |
| Behcet's Disease | |
| Bowel Obstruction | |
| Carcinoid of Gastrointestinal Tract | |
| Cholera | |
| Chronic Nonulcer dyspepsia | |
| Chronic Pancreatitis | |
| Colonic volvulus | |
| Colorectal cancer | |
| Cryptosporiosis | |
| Dysentery | |
| Entamoeba histolytica | |
| Enterocolitis | |
| Food intolerances | |
| Gallstones | |
| Gastric erosion | |
| Gastrointestinal Anthrax | |
| Giardia | |
| Migraine Equivalent | |
| dyspepsia | |
| Helicobacter pylori bacteria | |
| Hemolytic uremic syndrome | |
| Hirschsprung's disease | |
| Indigestion | |
| Intestinal pseudo-obstruction | |
| Megacolon | |
| Nonulcer dyspepsia | |
| Pancreatitis | |
| Peptic Ulcer | |
| Pyloric stenosis | |
| Rapid gastric emptying | |
| Dumping syndrome | |
| Shigellosis | |
| Small Intestine Cancer | |

TABLE I-continued

| TYPE OF DISORDER/MEDICAL CONDITION | TYPE OF SENSING PERFORMED |
|---|---|
| Sprue | |
| Stomach Cancer | |
| Viral digestive infections | |
| Viral dysentery | |
| Viral gastroenteritis | |
| Whipple's Disease | |
| Enteroviruses | |
| Malabsorption | |
| Class I obesity - basal metabolic index of 30-34.9 | |
| Class II obesity- basal metabolic index of 35-39.9 | |
| Class III obesity- basal metabolic index of 40 and higher | |
| IMMUNOLOGICAL DISORDERS | Radiographic, magnetic resonance imaging, computer tomography, bone densitometry, presence of effusion in joints or surrounding tissue, protein concentration and/or content in the joint or surrounding tissue, autoantibodies, antinuclear antibody, antibodies to double-stranded DNA, depressed serum complement, rheumatoid factor, creatine kinase, antinuclear antibodies, erythrocyte sedimentation rate C-reactive protein, uric acid, specific-IgE antibody to tested aeroallergens, serum tryptase, immune complexes in serum or deposited in affected tissues |
| Rheumatoid arthritis | |
| Autoimmune thyroid diseases | |
| Graves Disease | |
| Hashimoto's Thyroiditis | |
| Systemic Lupus Erythematosus | |
| Multiple Sclerosis | |
| Crohn's disease | |
| Psoriasis | |
| Psoriatic Arthritis | |
| Sympathetic ophthalmitis | |
| Autoimmune neuropathies | |
| Autoimmune oophoritis | |
| Autoimmune orchitis | |
| Autoimmune Lymphoproliferative Syndrome | |
| Antiphospholipid syndrome | |
| Sjogren's Syndrome | |
| Rheumatoid arthritis | |
| Scleroderma | |
| Lupus | |
| Addison's Disease | |
| Polyendocrine deficiency syndrome | |
| Polyendocrine deficiency syndrome type 1 | |
| Polyendocrine deficiency syndrome type 2 | |
| Guillain-Barre Syndrome | |
| Immune Thrombocytopenic Purpura | |
| Pernicious anemia | |
| Myasthenia Gravis | |
| Primary biliary cirrhosis | |
| Mixed connective tissue disease | |
| Primary Glomerulonephritis | |
| Vitiligo | |
| Autoimmune uveitis | |
| Autoimmune Hemolytic Anemia | |
| Autoimmune Thrombocytopenia | |
| Celiac Disease | |
| Dermatitis herpetiformis | |
| Autoimmune Hepatitis | |
| Pemphigus | |
| Pemphigus Vulgaris | |
| Pemphigus Foliaceus | |
| Bullous Pemphigoid | |
| Autoimmune Myocarditis | |
| Autoimmune Vasculitis | |
| Autoimmune eye diseases | |
| Alopecia Areata | |
| Autoimmune Atherosclerosis | |
| Behcet's Disease | |
| Autoimmune Myelopathy | |
| Autoimmune Hemophilia | |
| Autoimmune Interstitial Cystitis | |
| Autoimmune Diabetes Insipidus | |
| Autoimmune Endometriosis | |
| Relapsing Polychondritis | |
| Ankylosing Spondylitis | |

TABLE I-continued

| TYPE OF DISORDER/MEDICAL CONDITION | TYPE OF SENSING PERFORMED |
|---|---|
| Autoimmune Urticaria | |
| Paraneoplastic Autoimmune Syndromes | |
| Dermatomyositis | |
| Miller Fisher Syndrome | |
| IgA nephropathy | |
| Goodpasture syndrome | |
| Herpes gestationis | |
| OCULAR DISORDERS | |
| Myopia | |
| Hyperopia | |
| Astigmatism | |
| Corneal ulcer | |
| cataracts | |
| glaucoma-narrow angle or open angle | |
| diplopia | |
| macular degenaration | |
| retinal dystrophy | |
| Corneal flash burns | |
| Corneal abrasion | |
| retinitis pigmentosa | |
| amblyopia | |
| strabismus | |
| Corneal Dystrophies | |
| Fuchs' Dystrophy | |
| keratoconus | |
| lattice dystrophy | |
| map-dot-fingerprint dystrophy | |
| Presbyopia | |
| Age-related macular degeneration | |
| Uveitis | |
| Blindness | |
| DERMATOLOGICAL DISORDERS | |
| Acne | |
| Rosacea | |
| Eczema | |
| Psoriasis | |
| Hair Loss | |
| Hypertrichosis | |
| Seborrheic dermatitis | |
| Xerotic Skin | |
| Oily Skin | |
| Wrinkles | |
| Cellulite | |
| Vitiligo | |
| Radation induced damage | |
| urticaria | |
| ENDOCRINOLOGICAL DISORDERS | |
| Insulin Resistance | |
| Metabolic Syndrome | |
| Diabetes | |
| Type 2 Diabetes | |
| Type 1 diabetes | |
| impaired glucose tolerance | |
| Autoimmune diseases | |
| Autoimmune diseases | |
| Obesity | |
| hypoglycemia | |
| hyperthyroidism | |
| hypothyroidism | |
| amenorrhea | |
| dysmenorrhea | |
| perimenstrual syndrome | |
| hypercholesterolemia | |
| hypertriglycridinemia | |
| Cushing's disease | |
| Addison's disease | |
| malabsorption syndrome | |
| cold extremities | |
| hot flashes | |
| heat exhaustion | |
| Raynaud's syndrome | |
| hormonal disorders | |
| gout | |
| metabolic storage diseases | |

TABLE I-continued

| TYPE OF DISORDER/MEDICAL CONDITION | TYPE OF SENSING PERFORMED |
|---|---|
| GENITOURINARY DISORDERS | |
| Impotence | |
| Urinary Incontinence | |
| Cystitis | |
| Infertility | |
| Kidney conditions | |
| Kidney disease | |
| Kidney stones | |
| Glomerular Disease | |
| Glomerulonephritis | |
| Glomerulosclerosis (type of Glomerular Disease) | |
| Kidney cancer | |
| Diabetic nephropathy | |
| Lupus nephritis | |
| end-stage renal disease | |
| kidney failure | |
| Acute kidney failure | |
| IgA nephropathy | |
| Acute urinary conditions | |
| Urinary tract infections | |
| Urinary tract infections (child) | |
| Pyelonephritis | |
| nephrotic syndrome | |
| Childhood nephrotic syndrome | |
| Post streptococcal glomerulonephritis | |
| Goodpasture syndrome | |
| Nephrocalcinosis | |
| Kidney cysts | |
| Simple kidney cysts | |
| polycystic kidney disease | |
| Acquired Cystic Kidney Disease | |
| Autosomal dominant polycystic kidney disease | |
| Autosomal Recessive Polycystic Kidney Disease | |
| Diabetes Insipidus | |
| Autoimmune Diabetes Insipidus | |
| Alveolar Hydatid Disease | |
| Kidney Dialysis | |
| Primary amyloidosis | |
| Dialysis-related amyloidosis | |
| Hematuria | |
| Proteinuria | |
| Renal Tubular Acidosis | |
| Proximal Renal Tubular Acidosis | |
| Renal carbuncle | |
| Renal osteodystrophy | |
| Renal tuberculosis | |
| Tuberculosis | |
| Tuberous sclerosis | |
| Vesicoureteral reflux | |
| Wegener's granulomatosis | |
| Wilms' tumor | |
| Wilson's Disease | |
| Zellweger Syndrome | |
| Chronic kidney failure | |
| Nephritis | |
| Nephropathy | |
| Bladder Incontinence (Pregnancy) | |
| Penile candidiasis | |
| Polycystic kidney disease | |
| Delayed orgasm | |
| flaccid bladder | |
| spastic bladder | |
| Interstitial cystitis | |
| RENAL DISORDERS | hydrostatic pressure in renal tubular, glomerular filtration rate, electrolytes concentration including sodium, potassium and calcium in the tubules and renal vasculature, renin levels, aldosterone levels, erythropoietin levels, perfusion pressure, muscle tone of the bladder measured by myography, size of the bladder, hydrostatic pressure inside and outside the bladder |

TABLE I-continued

| TYPE OF DISORDER/MEDICAL CONDITION | TYPE OF SENSING PERFORMED |
|---|---|

PSYCHOLOGICAL DISORDERS

Insomnia
Sleep disorders
Depressive disorders
depression
clinical depression
Dysthymia
Bipolar disorder
Alcoholism
Schizophrenia
Nonaffective Psychosis
Somatization
Tourettes
autism
mental retardation
delusions
Smoking
Stress
Anorexia Nervosa
Alcohol abuse
Phobias
Anti-Social Personality Disorder
Borderline Personality Disorder
Social phobia
Eating disorders
Learning disabilities
addiction to illicit drugs
addiction to alcohol
Drug abuse
Generalized anxiety disorder
Attention Deficit Hyperactivity Disorder
Obsessive-compulsive disorder
Agoraphobia
Bipolar disorder
Panic disorder
addictive behavior such as gambling, sex
Bulimia nervosa
Binge eating disorder

INFLAMMATORY DISORDERS

Irritable Bowel Syndrome
Crohn's disease

PAIN DISORDERS migraine headaches with aura
migraine headaches without aura
menstrual migraines
migraine variants
atypical migraines
complicated migraines
hemiplegic migraines
transformed migraines
and chronic daily migraines
episodic tension headaches
chronic tension headaches
analgesic rebound headaches
episodic cluster headaches
chronic cluster headaches
cluster variants
chronic paroxysmal hemicrania
hemicrania continua
post-traumatic headache
post-traumatic neck pain
post-herpetic neuralgia involving the head or face
pain from spine fracture secondary to osteoporosis
arthritis pain in the spine
headache related to cerebrovascular disease and stroke
headache due to vascular disorder
reflex sympathetic dystrophy
cervicalgia
glossodynia
carotidynia
cricoidynia TABLE I-continued

| TYPE OF DISORDER/MEDICAL CONDITION | TYPE OF SENSING PERFORMED |
|---|---|
| otalgia due to middle ear lesion<br>gastric pain<br>sciatica<br>maxillary neuralgia<br>laryngeal pain<br>myalgia of neck muscles<br>trigeminal neuralgia<br>post-lumbar puncture headache<br>low cerebro-spinal fluid pressure headache<br>temporomandibular joint disorder<br>atypical facial pain<br>ciliary neuralgia<br>paratrigeminal neuralgia<br>petrosal neuralgia<br>Eagle's syndrome<br>idiopathic intracranial hypertension<br>orofacial pain<br>myofascial pain syndrome involving the head<br>myofascial pain syndrome involving the neck<br>myofascial pain syndrome involving the shoulder<br>my factual pain syndrome involving the back<br>chronic migraneous neuralgia<br>cervical headache<br>paratrigeminal paralysis<br>sphenopalatine ganglion neuralgia<br>carotidynia<br>Vidian neuralgia<br>causalgia<br>back pain<br>fibromyalgia<br>chronic fatigue syndrome | |
| METABOLIC STORAGE DISEASES | |
| lysosomal storage disorders<br>lipid storage diseases<br>glycogen storage diseases | |
| NEOPLASTIC DISORDERS | |
| metastatic cancer<br>benign growths<br>Aging Process<br>Radiation Induced Damage<br>Adjunct to conventional therapy including medication and/or surgery and/or psychiatric | |
| Enhancement of treatment efficacy<br>Limiting and minimizing adverse reaction and side effects<br>Hasten recovery<br>Enhancement of Normal Function and Physiology | |
| Improve coordination<br>Enhance memory<br>Increase physical endurance<br>Increase muscle strength<br>Increase speed in mobility<br>Cosmetics | |
| Breast enhancement<br>Breast Reduction<br>Removal of wrinkles of face, neck and body<br>Reduce fat around waist line<br>Flatten stomach<br>Increase resting muscle tone to abdominal muscles<br>Improve muscle tone in buttocks<br>Reduce and/or resolve cellulite<br>enhance calf muscles | |

We claim:

1. A method of alleviating an endocrinological condition in a patient suffering therefrom, said method comprising the steps of:
   placing an electrode in electrical contact with a target site of the patient, the target site including a cervical sympathetic nerve chain ganglion;
   detecting a bodily activity associated with the endocrinological condition via a sensor and generating a sensor signal; and
   activating the electrode to initiate application of an electrical signal to the target site in response to the sensor signal or adjusting application of an electrical signal to the target site in response to the sensor signal to alleviate the patient's endocrinological disorder;
   wherein the electrical signal has a voltage range of 0.1 μV to about 20 V and a frequency range of about 2 Hz to about 2500 Hz.

2. The method of claim 1, wherein the endocrinological disorder is related to the pancreas or the liver of the patient.

3. The method of claim 2, wherein the endocrinological disorder is at least one of hypoglycemia, Type I diabetes, Type II diabetes, or obesity.

4. The method of claim 1, wherein the bodily activity associated with the endocrinological condition is the level of at least one of glucose, liver enzymes, electrolytes, or hormones in the patient.

5. A method for alleviating an endocrinological condition related to the pancreas or liver of a patient suffering therefrom, said method comprising the steps of:
   placing an electrode in electrical contact with a target site of the patient, the target site comprising at least one cervical ganglion of the SNC;
   detecting a bodily activity associated with the endocrinological condition via a sensor and generating a sensor signal, the bodily activity associated with the endocrinological condition being the level of at least one of glucose, liver enzymes, electrolytes, or hormones in the patient; and
   activating the electrode to initiate application of an electrical signal to the target site in response to the sensor signal or adjusting application of an electrical signal to the target site in response to the sensor signal to alleviate the patient's endocrinological disorder, the electrical signal being an oscillating electrical operated at a frequency greater than about 1000 Hz, a pulse width between about 10 microseconds and about 1000 microseconds, and voltage between about 0.1 μV to about 20 V.

6. The method of claim 5, wherein the endocrinological disorder related to the pancreas or liver is at least one of hypoglycemia, Type I diabetes, Type II diabetes, or obesity.

7. The method of claim 5, wherein the thoracic ganglion is a T5-T12 ganglion.

8. The method of claim 5, wherein the cervical ganglion is at least one of a superior cervical ganglion, a middle cervical ganglion, an inferior cervical ganglion, or a cervicothoracic ganglion.

9. A method for alleviating an endocrinological condition related to the pancreas or liver of a patient suffering therefrom, said method comprising the steps of:
   placing an electrode in electrical contact with a target site of the patient, the target site comprising a cervical sympathetic ganglion;
   detecting a bodily activity associated with the endocrinological condition via a sensor and generating a sensor signal, the bodily activity associated with the endocrinological condition being the level of at least one of glucose, liver enzymes, electrolytes, or hormones in the patient; and
   activating the electrode to initiate application of an electrical signal to the target site in response to the sensor signal or adjusting application of an electrical signal to the target site in response to the sensor signal to alleviate the patient's endocrinological disorder;
   wherein the electrical signal has a voltage range of 0.1 μV to about 20 V and a frequency range of about 2 Hz to about 2500 Hz;
   wherein the endocrinological disorder related to the pancreas or liver is obesity.

10. The method of claim 1, wherein the electrode is placed on or in the at least one sympathetic nerve chain ganglion.

* * * * *